United States Patent
Leddy

(10) Patent No.: US 9,925,085 B2
(45) Date of Patent: Mar. 27, 2018

(54) METHOD AND APPARATUS FOR PENIS ENLARGEMENT

(71) Applicant: Patrick John Leddy, San Marcos, CA (US)

(72) Inventor: Patrick John Leddy, San Marcos, CA (US)

(73) Assignee: USA Life Nutrition, LLC, San Marcos, CA (US)

( * ) Notice: Subject to any disclaimer, the term of this patent is extended or adjusted under 35 U.S.C. 154(b) by 215 days.

(21) Appl. No.: 14/939,784

(22) Filed: Nov. 12, 2015

(65) Prior Publication Data

US 2016/0151226 A1 Jun. 2, 2016

Related U.S. Application Data

(60) Provisional application No. 62/085,413, filed on Nov. 28, 2014.

(51) Int. Cl.
*A61F 5/00* (2006.01)
*A61F 5/41* (2006.01)

(52) U.S. Cl.
CPC ..................... *A61F 5/41* (2013.01)

(58) Field of Classification Search
CPC ........................................................ A61F 5/41
USPC ..................................................... 600/38–41
See application file for complete search history.

(56) References Cited

U.S. PATENT DOCUMENTS

| | | | | |
|---|---|---|---|---|
| 5,707,341 | A * | 1/1998 | Mathewuse | A61F 5/41 600/39 |
| 5,836,864 | A * | 11/1998 | Clark, Jr. | A61F 5/41 600/38 |
| 2007/0093687 | A1* | 4/2007 | Hoefer | A61F 5/41 600/41 |
| 2015/0202109 | A1* | 7/2015 | Levin | A61H 1/0218 600/38 |

* cited by examiner

*Primary Examiner* — John Lacyk
(74) *Attorney, Agent, or Firm* — Robald R. Shea, Esq.

(57) ABSTRACT

A penis lengthening device comprises a traction chamber with tapered sidewalls configured to secure the penis within the chamber by forming a partial vacuum therein. A flexible air seal covers the upper portion of the traction chamber and extends over the penis. As the chamber is evacuated, the air seal tightens around the penis, creating an air seal to retain the vacuum within the chamber. Tensile force is transmitted through the chamber to the penis of the user. Alternative "light traction" embodiments utilize a condom-like device configured to attach to an elastic band, or to suspend weights therefrom. Larger tensile forces are applied for shorter periods of a few minutes up to an hour using the traction chamber embodiment, and smaller forces of 1-2 pounds are applied for longer periods of several hours using a light-traction embodiment. Alternate between the two methods throughout the day enhances its effectiveness.

20 Claims, 12 Drawing Sheets

METHOD AND APPARATUS FOR PENIS ENLARGEMENT

CROSS-REFERENCE TO RELATED APPLICATIONS

This application claims benefit of priority from, and incorporates by reference in its entirety, U.S. Provisional Application No. 62/085,413 "Method and Apparatus for Penis Enlargement" to Patrick Leddy, filed on Nov. 28, 2014.

BACKGROUND OF THE INVENTION

At one time, plastic surgery was reserved for "reconstructive surgery" following some disfiguring trauma. Even slower to develop have been surgeries, prosthetics and devices for enhancing gender related features. The modern prosthetic breast implant was invented in 1961 by plastic surgeons Thomas Cronin and Frank Gerow, and the first augmentation surgery was performed in 1962. By 2013, over a quarter-million American women a year were receiving breast implants.

In a similar manner, a man's identity, and sense of self-esteem and self-image, historically, have been connected to the size of his penis. This can be easily observed in the most ancient artistic pictures and sculptures. Male bravura, identifying themselves by their genitals in war time, is even found in the Bible I Samuel 25:22 & 34; I Kings 14:10, 16:11, etc. And in Ezekiel 23:20, the prophet Ezekiel uses graphic language to depict large male genitals as an object of amour for a lustful woman. From the beginning of our civilization, the human body has been an object of scientific, cultural, spiritual and aesthetic investigations. Ancient Egypt, both Pharaonic and Greco-Roman, has yielded much representational and artistic evidence for the nude human body. In Freud's psychosexual stages of human development, he centered on the sexual pleasure drive and immature (small) penis that he considered as the libidinal object of infantile sexuality in men. Many men are proud or ashamed of their penis-size, shape and performance. There is often anxiety about men's self-confidence due to the size of his penis and functionality. This directly relates to sexual performance, female satisfaction, intimacy and love.

Implants and Constrictive Rings for Erectile Dysfunction

FDA approved medications for erectile dysfunction are commonly known. Rings or constrictive devices to restrict blood flow are taught in U.S. Pat. No. 5,306,227 to Obson.

Surgical Implants for Erectile Dysfunction

U.S. Pat. No. 5,062,417 U.S. to Cowen appears to teach a surgical implant device for erectile dysfunction.

Vacuum Pumps for Erectile Dysfunction

The use of vacuum pumps for erectile dysfunction have been taught by U.S. Pat. No. 5,062,417 to Harris, U.S. Pat. No. 5,669,869 to Strom, U.S. Pat. No. 6,179,774 to Landry, U.S. Pat. No. 6,398,720 to Dabal; U.S. Pat. Nos. 6,458,073 and 7,083,570 to Bonthuys; U.S. Pat. No. 6,659,938 to Orlowski; U.S. Pat. No. 6,659,938 to Byon. For example, U.S. Pat. No. 6,398,720 to Dabal describes a device which is "useful for assisting in causing an erection in human males." Dabal, col. 1, lines 48-49. "The device is bulb-shaped when in its closed configuration by virtue of its being comprised of two semi-bulbular members. It is the closed configuration that is employed when the device is to be used for assisting in the achievement of an erection. The device has a semi-circular upper portion 30, a flat lower portion 32, and sidewall portions 34A and 34B that are angled inwardly from the semicircular upper portion and which terminate at the flat lower portion." Dabal, col. 2, lines 30-46. "The lip on the flat lower portion is shaped to fit up against the pubic bone." Dabal, col. 2, lines 56-57. "One particular advantage of a device according to the invention is that it is contoured to prevent any portion of the skin of the penis from contacting the walls of the device." (Dabal, col. 4, lines 54-59). Some such devices have achieved FDA approval for erectile dysfunction. However, these patents are directed only to enhancing male erection (and/or volumizing with blood), not actual lengthening of the penis (via traction/stretching).

Pump Enlargement

Vacuum pump applications for penis enlargement have been taught by U.S. Pat. Nos. 5,536,233; 5,676,634; and 5,695,445 to Khouri. It is uncertain, however, that such devices are capable of producing a permanent change in the size of the male penis.

Anatomical Limitations to Penis Size

The suspensory and fundiform ligaments anchor the penis to the pelvic region. Although much of the penis is visible as extending outside the body, a portion of the penis is disposed seven to ten centimeters deep within the male's pubic region. This internal part is anatomically known as the crus of the penis (crus corporis cavernosi penis). It is largely the suspensory and fundiform ligaments that retain a large percent of the penis "inside" of the male body. Accordingly, these ligaments may be responsible for limiting the length of the penis by one to two inches, and sometimes even more.

Surgical Enlargement

In the 1970s, a group of doctors in Kent, England conducted a study on surgical lengthening of the penis using sixty two volunteers with the approval of their wives. Thirty-two underwent surgical lengthening of the penis and thirty-two were used as controls. The technique presumably involved severing of the suspensory and fundiform ligaments. The average increase in penis length was around 2.0-2.5 cm.

Before starting the experiment the wives were asked to give their opinion about the size of their husbands' penises. 87% said they did not understand why their husbands decided to enlarge their penis when its size seemed adequate for its purpose. The same question was asked after the experiment, and this time, 67% of women had changed their opinion. Now, the women attributed superior quality of sexual intercourse to the larger penis, incomparable to the previous performance. They claimed that now they were able to reach a level of pleasure never imagined. Going from −87% to +67% is an impressive statistical change.

U.S. Pat. Nos. 7,584,757 and 8,291,914 to Kravosky disclose a surgical technique for lengthening the penis, which includes cutting the fundiform and suspensory ligaments. Post-surgery activity requires wearing weights (stretching physiotherapy exercises).

Ligament Stretching

With regard to permanently lengthening the penis without surgery, anyone who has conducted stretching exercises such as "touching their toes" daily will appreciate that ligaments can be stretched over time without surgery. Various attempts have been made to apply this principle to stretching the suspensory and fundiform ligaments of the penis to achieve penal enlargement.

U.S. Pat. Nos. 7,086,998 and 7,448,989 to Dana teach a traction devices that attaches to the penis through mechanical devices configured to suspend weight from the penis.

U.S. Pat. No. 7,566,299 to Montgomery discloses a "penis enlargement device comprising an end ring 14 and a plurality of stealth rings 42." (Col. 5, lines 19-20). The end ring has a "curved tapered outer sidewall 18 [which] is advantageous in that allows the wearer of the end ring 14 to be discreet while undergoing a penis enlargement session. This is particularly advantageous if the enlargement session is to be carried out in public." (Col. 5, line 6-10.) A principle function of Montgomery, therefore, appears to be a traction device which can be concealed under the clothing.

U.S. Pat. No. 8,162,819 to Adams addresses limitations of vacuum traction devices. According to Adams, "Suction devices are also cumbersome and impractical to wear on a prolonged basis, have limited effectiveness, and pose a number of risks. Suction devices produce localized compressive forces that may cause localized ischemia. Vacuum seals with pressure over 20 mm Hg can obstruct capillary flow and inhibit tissue perfusion. Suction devices often come with warnings that the devices should not be used for periods exceeding 20-30 minutes, which may be insufficient to achieve the desired result. Use of suction devices can also result in the thickening of the skin and accumulation of fluid in the superficial layers of the skin and subdermis. The skin of the penis is hypermobile, and only very loosely connected to deeper connective tissues and structures that comprise the erectile tissues of the penis. The skin of the penis can readily separate from the fibrous connective tissue capsule, which encloses the erectile tissue of the penis when externally applied suction forces are applied to the penis. Also, any suction forces applied to the penis has a proportionately larger effect on the skin, and the forces on the deeper structures diminish dramatically. The increase in the surface area of the skin causes the suction forces to be applied mainly to the skin, not to the erectile tissue and the surrounding capsule of the cavernosal tissue. As a result, the skin can be thickened as fluid is extravasated and there is typically no, or only a limited enlargement, of the underlying erectile tissues of the penis. Use of suction devices may also cause the separation of the skin from the sub-dermis and the formation of seromas or blisters on the penis. The application of suction devices to the penis may also cause the extravasation of red blood cells out of the vascular spaces and into the extracellular compartments. If vacuum devices are applied for extended periods of time, this may lead to a significant pigmentation of the penis. Also applying a suction device repeatedly may cause the deposition of large amounts of iron and other hemoglobin degradation products in the tissue of the penis causing hemosiderosis, which ultimately results in fibrosis. Furthermore, erectile dysfunction may result from prolonged use of these devices." Adams, Col. 2, line 44-Col. 3, line 15. Adams proposes a non-vacuum device to avoid these limitations.

Other patent applications have attempted to regulate vacuum traction devices to reduce the possibility of ischemia, pain; pallor (color change due to lack of blood flow); pulselessness, paresthesia (tingling when a limb "falls asleep"), paralysis and poikilothermia (failure to maintain temperature). A pressure control for pump devices are disclosed by U.S. Pat. No. 5,782,621 to Harris in conjunction with vacuum devices for erectile dysfunction. U.S. Pat. No. 5,707,341 to Mathewuse discloses a cone shaped wrap to prevent swelling of the glans-penis in vacuum-type traction devices. U.S. Pat. No. 5,836,864 to Clark also addresses apparatus to limit swelling of the penis in vacuum traction devices. Notwithstanding the advances of these patents, limitations persist.

SUMMARY OF THE INVENTION

There exists therefore a need for a safe and effective method and apparatus for stretching the suspensory and fundiform ligaments to permanently affect the lengthening of the penis.

DETAILED DESCRIPTION

Figure 1:
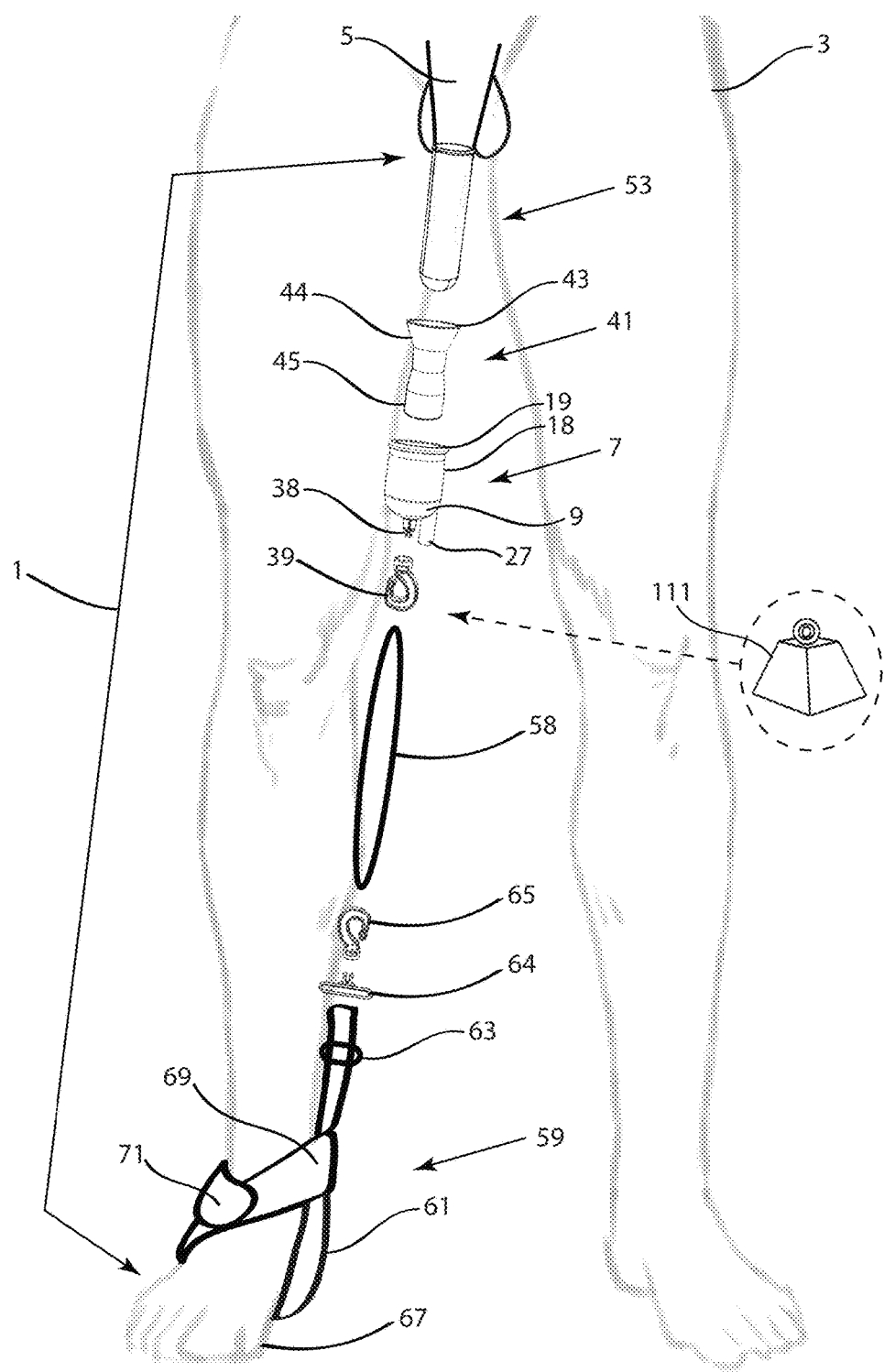
FIG. 1 depicts an exploded view of an embodiment of the traction device 1 described herein as worn by a user 3, including the individual components thereof.
Figure 2:
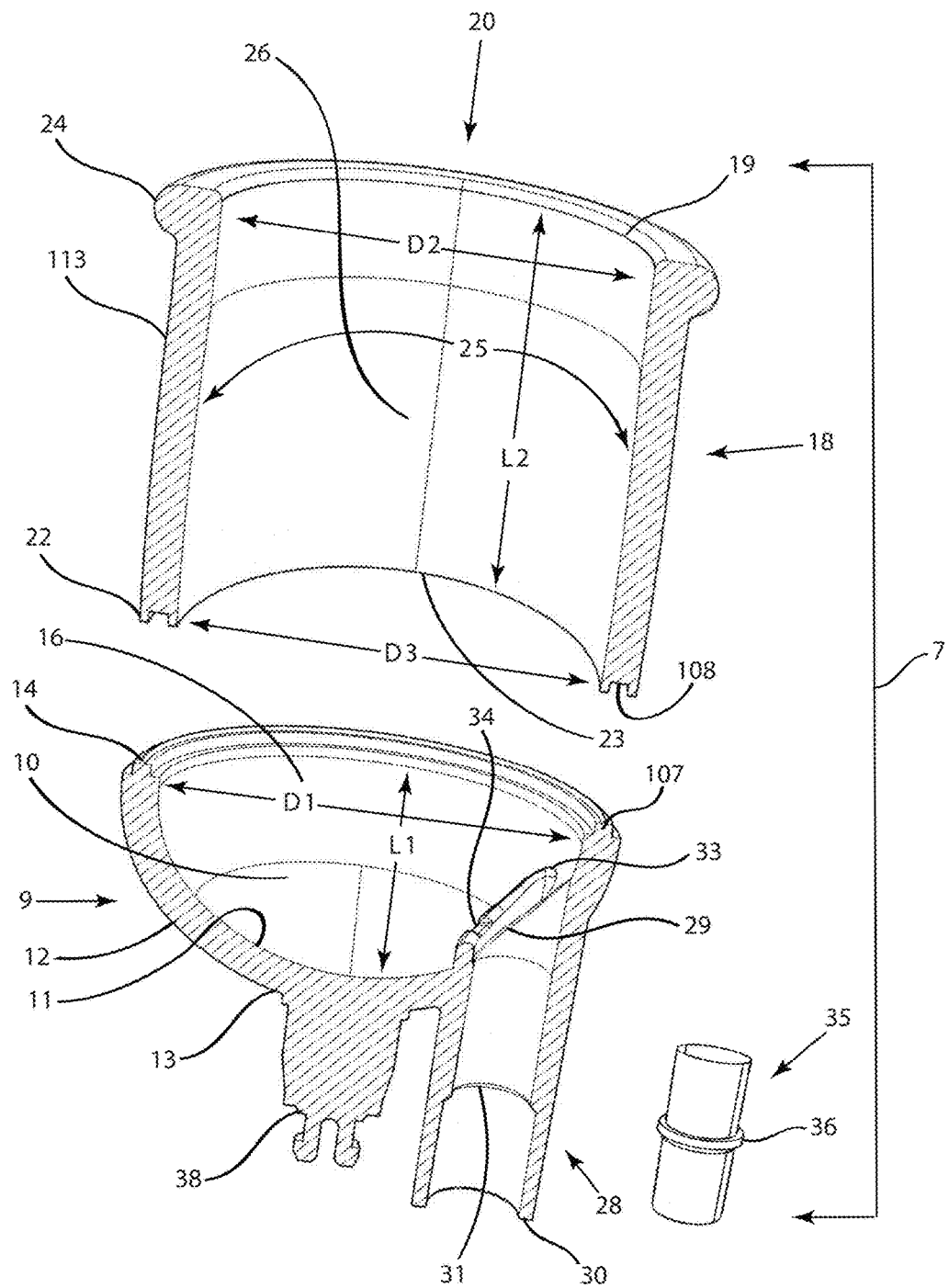
FIG. 2 depicts an exploded view of the traction chamber 7 depicted in FIG. 1, including greater detail on the dimensions of the dome 9 and frustum 18, and the tongue 107 and groove 108 design.

FIG. 1 depicts an exploded view of an embodiment of a Traction Device 1 for lengthening, enlarging or extending the penis 5 of a user 3 according to an embodiment of the present invention. The embodiment of the Traction Device 1 of FIG. 1 may include, as depicted in exploded view, a standard gel-flex sleeve 53 worn on the penis 5 of a user 3. A traction chamber 7 comprises an upper Frustum 18 and a lower Inverted Dome 9. In an embodiment, the frustum and dome are permanently joined by spin welding or some other means during manufacture to form a unitary traction chamber 7. The traction chamber 7 further comprises an airlock port assembly 27 for withdrawing air from the traction chamber 7. Referring also to FIG. 2, the airlock port assembly 27 includes a hollow tubular airlock port 28 with a check-valve 35 disposed therein. The airlock port 28 is a tubular structure with a proximal end 29 coupled to the dome 9 and the distal end 30 extending outward from the dome.

A snap fixture 38 disposed at the tip of the inverted dome 9 is configured to engage with a swivel hook 39 discussed in greater detail below. The snap fixture 38 may be formed as a unitary piece with the inverted dome 9 through injection molding, or coupled to the exterior surface of the dome 9 through known means, such as epoxy or sonic welding.

Referring to FIGS. 1, 3, 5A, 5B and 5C, the gel flex air seal 41 is a tubular flexible structure which is stretched over the tubular lip 24 at the proximal end 19 of the frustum to secure an air seal.

Figure 6:
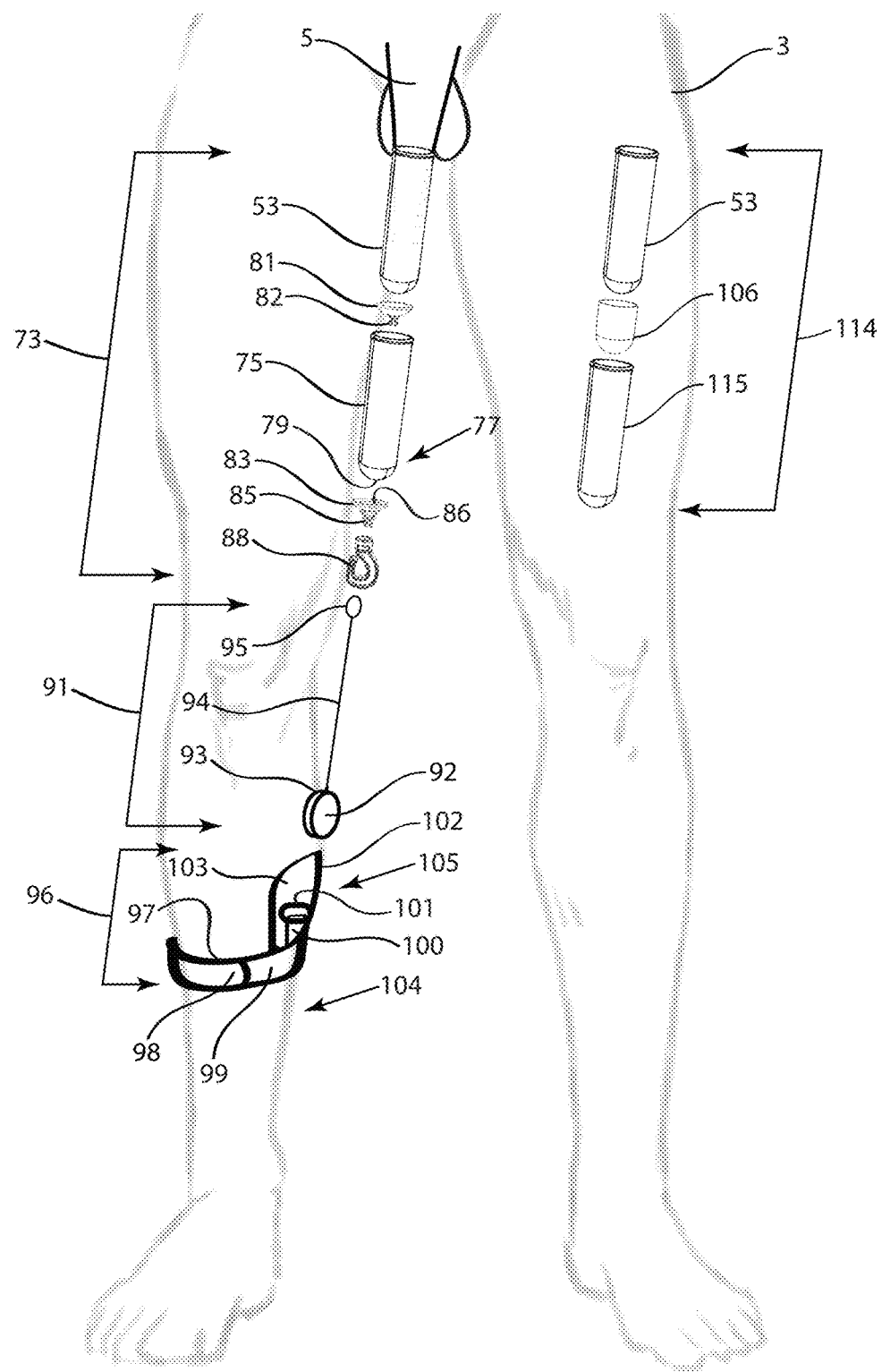
FIG. 6 depicts an embodiment of the light traction device 73 for use with a calf strap assembly 96 and continuous tension device 91, and alternative (embedded weight 106 embodiment of a light tension device.)

In embodiments utilizing tension bands 58 (FIG. 1) the traction device can be used in conjunction with an opposing tensile device including, but not limited to, a foot strap assembly 59 shown in FIG. 1, or a calf strap assembly 96 depicted in FIG. 6. For illustrative purposes, the traction embodiment 1 of FIG. 1 is depicted as being used in conjunction with elastic bands 58 and a foot strap assembly 59.

One or more elastic band(s) 58 are attached to the swivel hook 39 and the foot strap hook 65, thereby exerting tension on the penis 5. As depicted in FIG. 1, a weight 111 may be used in place of the elastic bands.

Operation of the Traction Device

Referring generally to FIG. 1, in operation, the gel flex sleeve 53 is initially in a "rolled" state, resembling a packaged condom, and is advantageously applied onto the penis 5 by unrolling it in a manner similar to the application of a condom. When removing the gel flex sleeve 53, therefore, a user 3 will advantageously roll the gel flex sleeve downward to again resemble a packaged condom, thereby ensuring ease of re-use the next time it is worn. After applying the gel flex sleeve 53 to the penis 5, the penis 5 is inserted through the gel flex air seal 41 and into the traction chamber 7.

Figure 9:
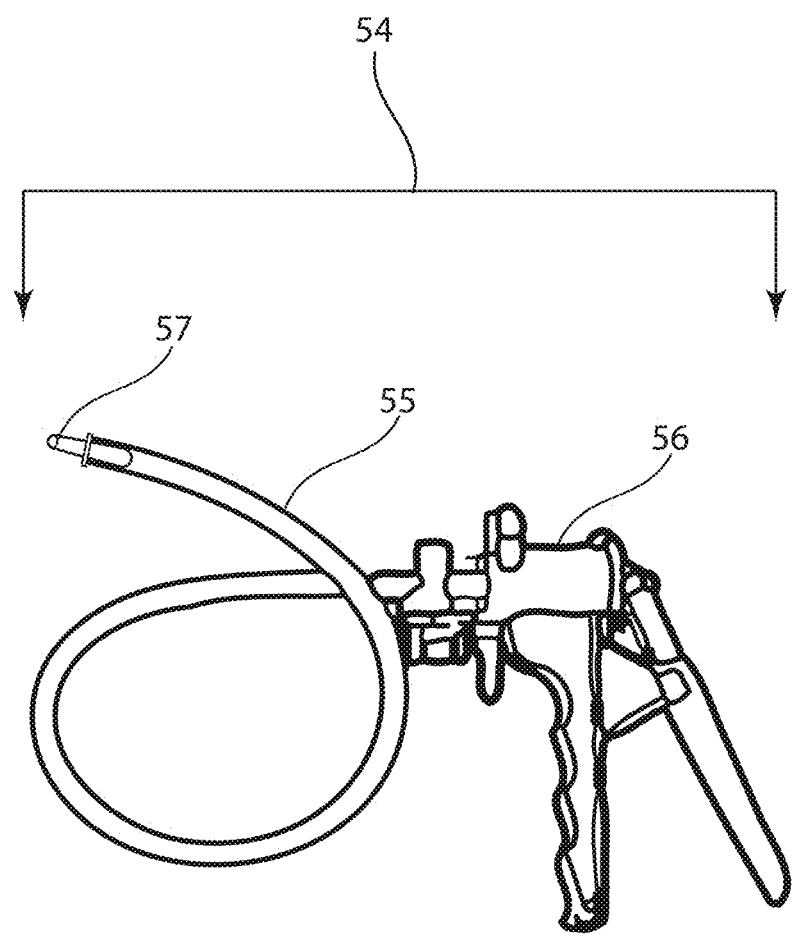
FIG. 9 depicts an embodiment of a vacuum pump assembly used to withdraw air from the traction chamber.

Referring briefly to FIG. 9 in conjunction with FIG. 1, a vacuum pump assembly 54 comprises a pump 56 coupled to a vacuum hose 55. The vacuum hose terminates in a vacuum nipple 57 configured to interface with the vacuum port assembly 28 to withdraw air from the traction chamber 7. In operation, after insertion of the penis 5 through the seal 41 and into the traction chamber 7 (FIGS. 1-3), the vacuum nipple 57 is engaged with the airlock port assembly 28, and the vacuum pump 56 is actuated to partially evacuate the traction chamber 7. During the evacuation process, the penis 5 expands to fill the empty space within the traction chamber 7. When the desired pressure is reached, the vacuum pump nipple is released from the valve assembly.

Returning to FIG. 1, the foot strap assembly 59 is attached to the foot 67 of a user 3, and elastic bands 58 are attached between the swivel hook 39 and the foot strap hook 65. A disadvantage of tension embodiment is that a user may move or shift posture or position, altering the distance between the two hooks 39, 65. If the user is at home wearing a bathrobe or other pants-free mode of dress, sitting and crossing one's legs may reduce the distance between the hooks 39, 65. However, if the user were wearing trousers, the same motion may increase the distance between the hooks 39, 65, producing excessive tension on the penis. One solution for tension embodiments is to incorporate less tension than optimal or desired, so that movement or posture that increases tension to an unexpected level remains tolerable. In an alternative embodiment depicted in FIG. 1, one or more weights 111 may be suspended from the swivel hook 39 in place of, or in conjunction with an elastic band 58.

The Traction Chamber

Figure 3:
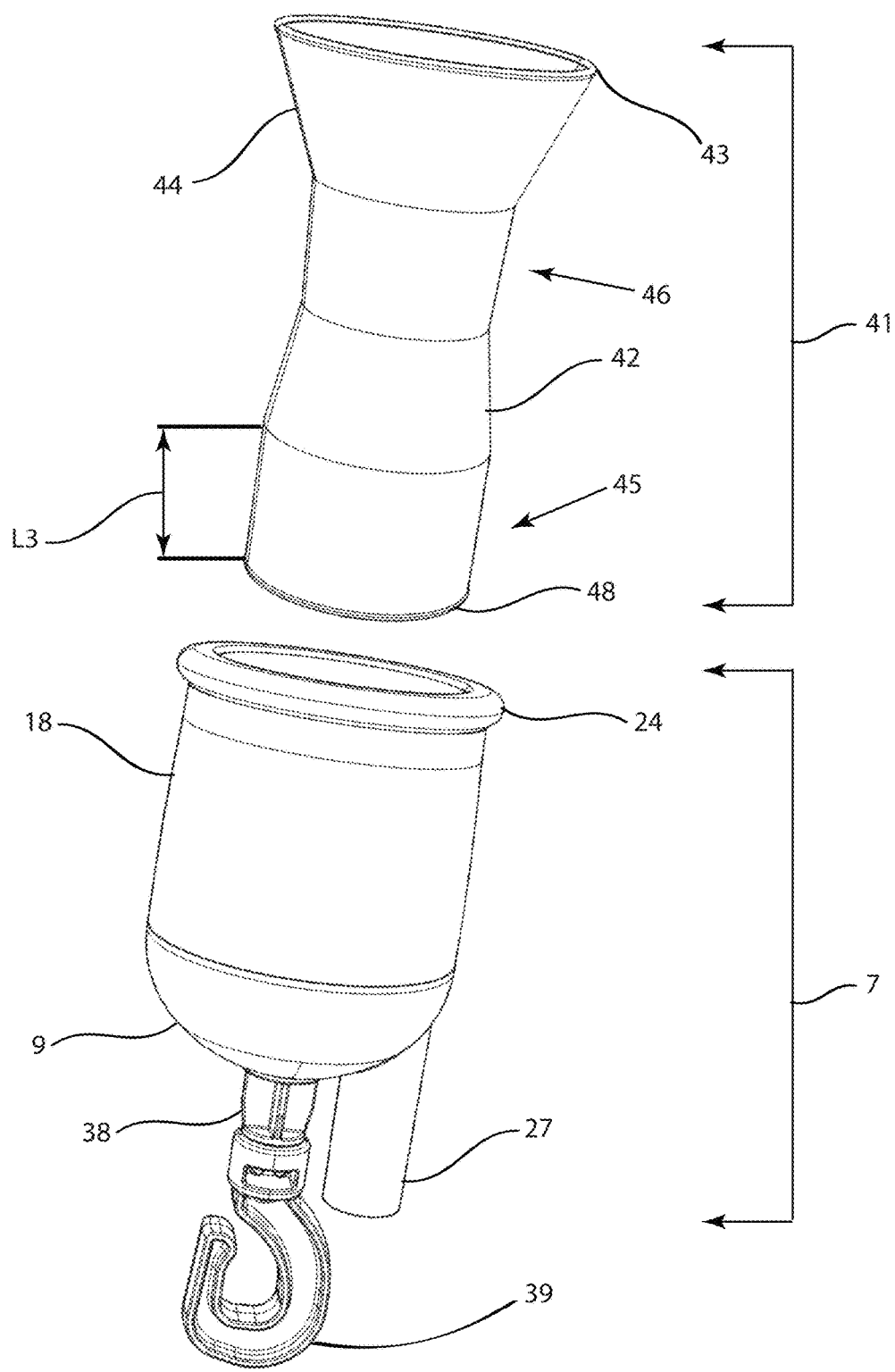
FIG. 3 depicts the traction chamber of FIGS. 1 and 2 in an assembled state, with the gel flex seal 41 positioned in exploded view above the traction chamber.

FIGS. 2 and 3 respectively depict exploded and assembled views of the traction chamber 7. Referring principally to FIG. 2, the traction chamber 7 comprises an inverted dome 9 which, in final assembly, is securely coupled to the frustum 18 in an air tight connection. FIG. 2 depicts an embodiment where joining of the frustum 18 with the dome 9 may be achieved by tongue 107 and groove 108 connection. The assembled traction chamber 7 depicted in FIGS. 1 & 3 may be permanently assembled through known means such as spin welding, sonic welding or epoxy. In an alternative embodiment, the coupling between the dome 9 and frustum 18 may be a releasable coupling such as through threaded interface. In any embodiment, the connection of the dome 9 to the frustum 18 comprises an airtight seal. A snap fixture 38 is disposed on the exterior surface 12 of the dome. The snap fixture may be formed in the injection molding process as a single integral part of the dome 9, or may be securely coupled to the exterior surface of the dome 9 through known means, such as epoxy, sonic welding, spin welding, or other known means. A swivel hook 39 comprises a connector which is configured to attach to the snap fixture 38.

The Frustum

Referring still to FIGS. 2 and 3, the frustum 18 of the traction chamber 7 comprises a hollow tubular interior 26 extending from the proximal opening 20 at the proximal end 19 of the frustum to the distal "opening" 23 at the distal end 22 of the frustum. The interior area 26 is sized to accommodate insertion of a human penis 5 (FIG. 1). Although the interior sidewalls 25 of the frustum may appear, on first glance, to define a cylindrical area, in a preferred embodiment, the interior sidewalls 25 preferably exhibit a positive taper defining a conic frustum (or functionally equivalent shape) rather than a cylinder. The "taper" of the sidewall 25 is such that the diameter D2 of the proximal opening 20 is smaller than the diameter D3 of the distal opening 23 of the frustum 18. The term "positive taper" is therefore used herein to represent an interior shape wherein a diameter near the proximal end 19 is smaller than the diameter of the interior near the distal end 22 of the frustum 18.

Because frictional and forcible contact between the sidewalls and the penis is essential to the traction chamber embodiment, the taper must not be so great as to forfeit contact with the penis, or reduce forcible contact to the point that the frictional and forcible engagement is compromised. The function of the traction device depends on a forcible connection with the penis to resist pulling the traction device free from the penis. Moreover, if the sidewalls diverge at too great an angle, the penis may be subject to prolonged exposure to reduced air pressure, potentially resulting in many undesired physiological side effects. Therefore, a critical feature of the traction chamber embodiment is that the positive taper of the frustum is configured such that the sidewalls maintain secure contact and pressure with the penis throughout the length of the frustum.

According to a preferred embodiment, therefore, the angle of the sidewall relative to the axis of the frustum is less than 4°. In a more preferred embodiment, the angle of the sidewall relative to the axis of the frustum is less than 3°. In yet a more preferred embodiment, the angle of the sidewall relative to the axis of the frustum is within a few tenths of 2.1°, which is equal to a 4.2° angle of intersection between opposing sidewalls.

The foregoing angle can be achieved by the following dimensions of the frustum: The diameter D2 of proximal opening 20 of the frustum 18 is in the range from 3.25 cm to 3.5 cm, and even more preferably 3.38 cm. However, human beings vary in size, and frustums 18 having a smaller opening diameter D2 in the range of 2.25 cm to 3.25 cm are envisioned. Larger frustum openings 20 in the range of 3.5 cm to 5.5 cm are also envisioned. Although custom sized openings can be designed to accommodate any user, the range 2.25 cm to 5.5 cm is sufficient for almost all potential users.

Still referring to FIG. 2, according to a preferred embodiment, the distal edge 22 of the frustum 18 abuts the proximal end 14 of the inverted dome 9. (Although the two pieces 9, 18 are advantageously permanently joined by spin welding or some other permanent means as noted). Therefore, the cross sectional diameter D3 of the distal end 23 of the frustum will preferably align with, and match the size D1 of the opening 16 of the inverted dome 9. In a preferred embodiment, the diameter D3 is in the range of 3.55 cm to 3.78 cm, and even more preferably within a few millimeters of 3.66 cm. However, larger embodiments are envisioned wherein the diameter D3 of the distal opening 23 of the frustum 18 is in the range of 3.78 cm to 5.0 cm. Additionally, smaller embodiments are also wherein the diameter D3 is in the range of 2.75 cm to 3.55 cm. Regardless of the dimension, the abutting openings 16, 23 preferably have identical diameters, and are preferably aligned. The foregoing dimensions are not intended as a limitation, but are offered as examples to enable one skilled in the art to make and use an embodiment suitable for over 90% of the population, and probably over 99%.

As illustrated in FIG. 2, the length L2 of the frustum 18 is defined as the distance between the proximal opening 20 (or the proximal edge 19) and the distal opening 23 (or distal edge 22) of the frustum 18. To achieve a specific angle at which the sidewalls 25 intersect, the diameter of the openings and the angle of the sidewalls will mathematically dictate the length "L2" of the frustum. Assume, for example, a proximal opening 20 having a diameter of 3.38 cm and a distal opening 23 having a diameter of 3.66 cm and a sidewall angle of 4.2° (relative to the opposing sidewall, or 2.1° relative to the axis of the frustum). These values will dictate the length of a frustum L2 at approximately 3.81 cm, which defines a preferred embodiment. However, shorter frustums having a length L2 in the range of 2.0 cm to 3.71 cm are envisioned for smaller users, and longer frustums having a length L2 in the range of 3.82 cm to 8.0 cm are also envisioned.

The use of the term "frustum" is not intended to limit the taper of the frustum 18 to a linear intersecting of the interior sidewalls 25. Curved or other non-linear sidewall contours are envisioned which functionally duplicate the effects of the linear taper of the interior sidewalls 25 described above.

The Inverted Dome:

Still referring to FIGS. 2 and 3, the inverted dome 9 comprises a rounded (concave) interior surface 11 contoured to interface with the glans of the user's penis 5. The exterior surface 12 of the inverted dome 9 comprises a convex contour. The opening 16 has a diameter D1. The depth L1 of the dome interior 10 is defined by a line extending from the opening 16 at the proximal end 14 of the dome to the interior surface 11 at the deepest point of the dome (farthest from the opening 16). The contour of the interior surface 11 generally comprises a "negative taper" wherein the interior diameter progressively decreases moving inward away from the opening 16 and toward the tip of the dome. However, embodiments are envisioned in which the interior contour of the dome comprises a positively tapered segment proximate the opening 16, configured to engage the glans in a "head lock" to increase traction. Because the frustum 18 and the dome 9 form a single unitary member after assembly, the "head lock" segment may alternatively be formed on the interior surface 25 of the frustum, proximate and distal edge 22 of the frustum.

The interior area 10 of the inverted dome 9 should be small enough to ensure that contact is maintained between the glans of the penis 5 and the interior surface 11, thereby reducing the possibility of excessive or prolonged swelling of the glans, which may induce localized ischemia, edema, or other deleterious effects of a reduced air pressure environment.

A trial traction device was developed and successfully utilized by volunteers. The trial traction device had the following dimensions: A diameter D1 of the opening 16 at the proximal end 14 of the inverted dome 9 was measured at 3.66 mm. As illustrated in FIG. 2, the "depth" of the dome interior 10 is measured from the opening 16 at the proximal end 14 of the inverted dome to the farthest point on the interior surface 11. In the trial traction device, the depth of the dome interior 10 was measured at 1.59 cm. The recitation of these specific dimensions is not intended as a limitation, but as an example of dimensions of the inverted dome which will be useful to many users. Domes having greater or smaller dimensions are envisioned.

The Airlock Port Assembly

Figure 4:
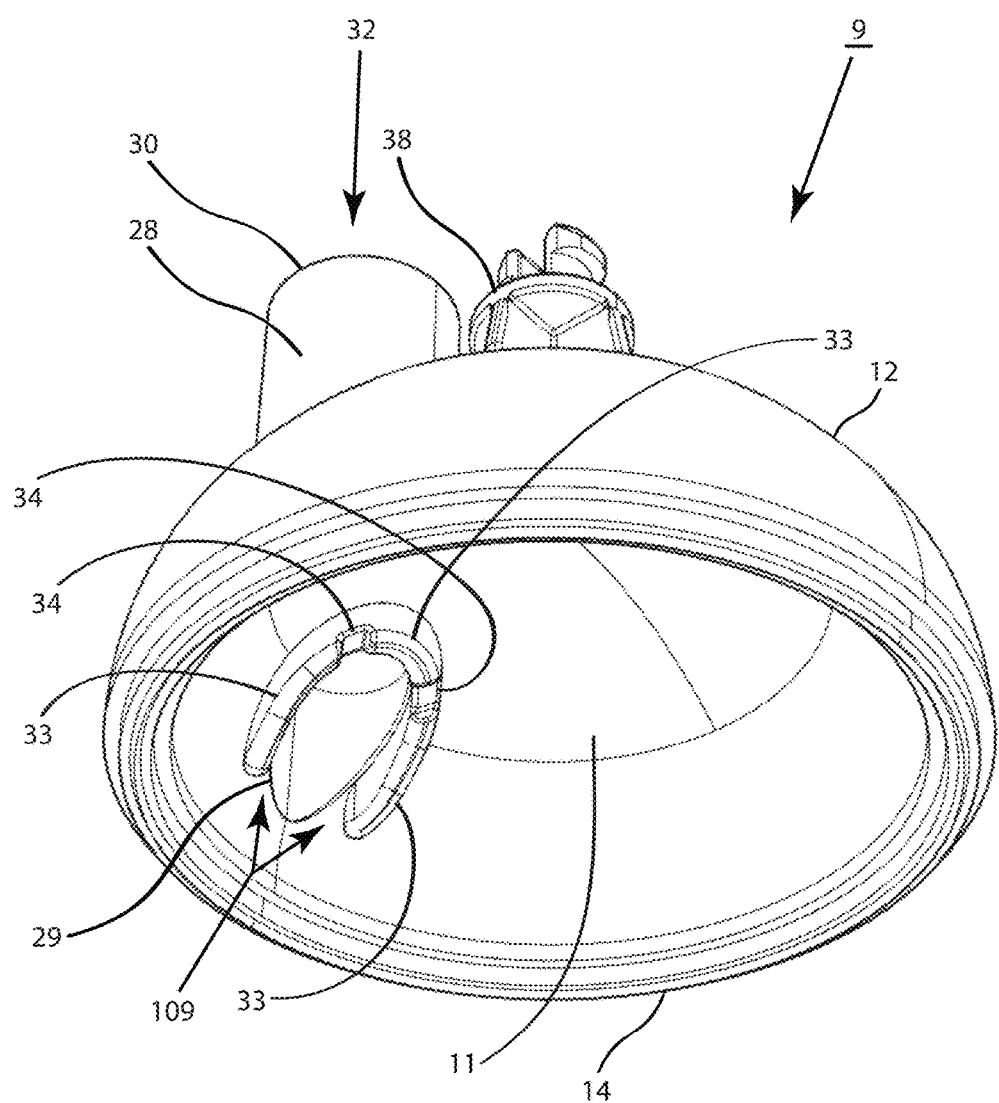
FIG. 4 depicts an upside down view of the dome 9, with details of the airlock tissue barrier 33.

As depicted in FIGS. 2, 3 and 4, the airlock port assembly 27 comprises an airlock port 28 advantageously formed as a tubular member with a proximal end 29 coupled to the dome 9 of the traction chamber 7, and a distal end 30 extending outward from the traction chamber 9. In the embodiment of FIGS. 2, 3 and 4, the dome 9 and airlock port 28 are formed as a single contiguous piece through the injection molding process during manufacture. Embodiment are also envisioned, however, in which the airlock port 28 is formed separately from the dome 9, and coupled to the dome through known means, such as threaded assembly, spin welding, sonic welding, epoxy, or combinations thereof. In any embodiment, the airlock port 28 forms a secure (airtight) seal with the dome.

In assembly, the check valve 35 (FIG. 2) is inserted into the airlock port 28, and permanently secured therein by known means such as epoxy, spin welding, or sonic welding, or combinations thereof, thereby forming the airlock port assembly 27. In operation, a partial vacuum is induced within the traction chamber 7 by withdrawing air through the airlock port 28.

Referring still to FIG. 2, in an embodiment, the airlock port 28 includes an interior airlock shelf 31 against which the check valve 35 abuts during assembly. In the embodiment depicted in FIG. 2, the check valve 35 comprises a check valve shelf 36, which is the specific structure that abuts against the interior airlock shelf 31. The interior airlock shelf 31 provides structural resistance preventing the check valve 35 from being sucked into the traction chamber 7 when a partial vacuum is formed within the chamber. Additionally, the abutment of the check valve shelf 36 with the interior shelf 31 provide surface area for the deposition of an airtight sealant (or abutting structures for sonic or spin welding), and also controls the exact depth of the check valve 35 within the airlock port 28, ensuring that the valve assembly will reliably interface with the vacuum nipple 57 at the end of the vacuum hose (FIG. 9).

Another advantage of the embodiment comprising a check valve shelf 36 to abut is depicted in FIG. 2 is that, in addition to the structural resistance (and any weld or sealant) of the interior airlock shelf 31 against the check valve shelf 36, sealant may be applied between the interior sidewall of the airlock port 28 and the portion of the check valve 35 that extends beyond the interior airlock shelf 31, enhancing the airtight integrity.

The Airlock Tissue Barrier

Referring to FIGS. 2, 3 and 4, it can be readily appreciated that, as air is withdrawn from the traction chamber 7, tissue of the expanding penis 5 could easily be sucked into air intake opening 32 of the airlock port 28, blocking further air passage through the air lock port 28, and potentially damaging the tissue of the penis 5 through excessive vacuum differential between the dome interior and the air intake 32. To prevent this, a tissue barrier 33 is disposed adjacent to the air intake opening 32. FIG. 4 discloses a tissue barrier 33 comprising a horseshoe shape surrounding the opening 29 of the airlock port. The airlock tissue barrier 33 impedes the tissue from the glans penis from being sucked into the air intake opening 29. The tissue barrier can be any size, but in a preferred embodiment is from 3 to 10 mm in height. As further depicted in FIG. 4, the airlock tissue barrier 33 is curved in a horseshoe shape, surrounding the air intake opening 32 on three sides. The "horseshoe opening" 109 of the tissue barrier 33 faces the sidewall of the inverted dome 9. This orientation reduces the likelihood that tissue from the glans will enter the horseshoe shaped opening 109 and be drawn into the air intake opening 29.

Air baffles 34 disposed on the top surface of the tissue barrier 33 to ensure a path for air-flow during the evacuation of the traction chamber 7. Alternative embodiments are envisioned wherein the baffles 34 are formed in the bottom of the airlock tissue barrier 33, immediately adjacent the interior surface 11 (FIGS. 2, 4) of the dome 9.

The Gelflex Air Seal

FIGS. 1 and 3 depict a Gel flex air seal 41, which is preferably made of a flexible, stretchable, rubber-like material such as latex or medical-grade Versaflex. The gel flex air seal 41 comprises a generally tubular structure. Beginning at the proximal edge 43, the gel flex air seal comprises a sequence of segments, including a spout 44 which extends into a neck 46, which extends into a drum head 42, which extends into a skirt 45 terminating at the distal end 48 of the gel flex air seal. Although a slight angle of taper is shown between the various segments 44, 46, 42, 45 of the gel flex air seal 41, the distinction between these segments, while functional, is nevertheless somewhat arbitrary. Embodiments comprising more, or fewer segments are envisioned, including a straight tubular gel flex air seal 41 effectively disclosing one continuous segment.

In the embodiment of FIG. 3, the spout 44 in FIG. 3 is tapered (having the largest diameter nearest the proximal edge 43) to allow ease of application by a user. Prior application, the spout 44 is advantageously arranged into a "rolled" configuration, similar to a packaged condom. It is applied by unrolling it onto the penis 5, in a manner similar to application of a condom. When the user 3 removes the traction apparatus 1, the spout 44 of the gel flex seal 41 is advantageously "rolled" downward to again resemble a packaged condom, facilitating re-use with the greatest ease of application. The neck segment 46 may also be included in the rolling and unrolling process.

Referring principally to FIG. 3, to complete the assembly of the traction unit 1 prior to application by a user 3, the skirt 45 of the gel flex seal 41 is stretched outward and pulled-down over the tubular lip 24 at the proximal edge 19 of the frustum 18. In use, the tensile force exerted on the traction unit 1 by the elastic band(s) 58 or exerted by the weight 111 (FIG. 1) operate to pull the traction chamber 7 free from the gel flex seal 41. However, after the skirt 45 of the gel flex seal 41 is pulled over the exterior surface 113 of the frustum 18, the tension of the stretched skirt 45 imparts an annular tensile force upon the exterior surface 113 (FIG. 2) of the frustum 18, enhancing the frictional engagement between the skirt and the frustum. This engagement serves to secure the gel flex seal 41 to the frustum 18, resisting the tensile force which works to pull the frustum free from the gel flex seal.

Figure 5A:
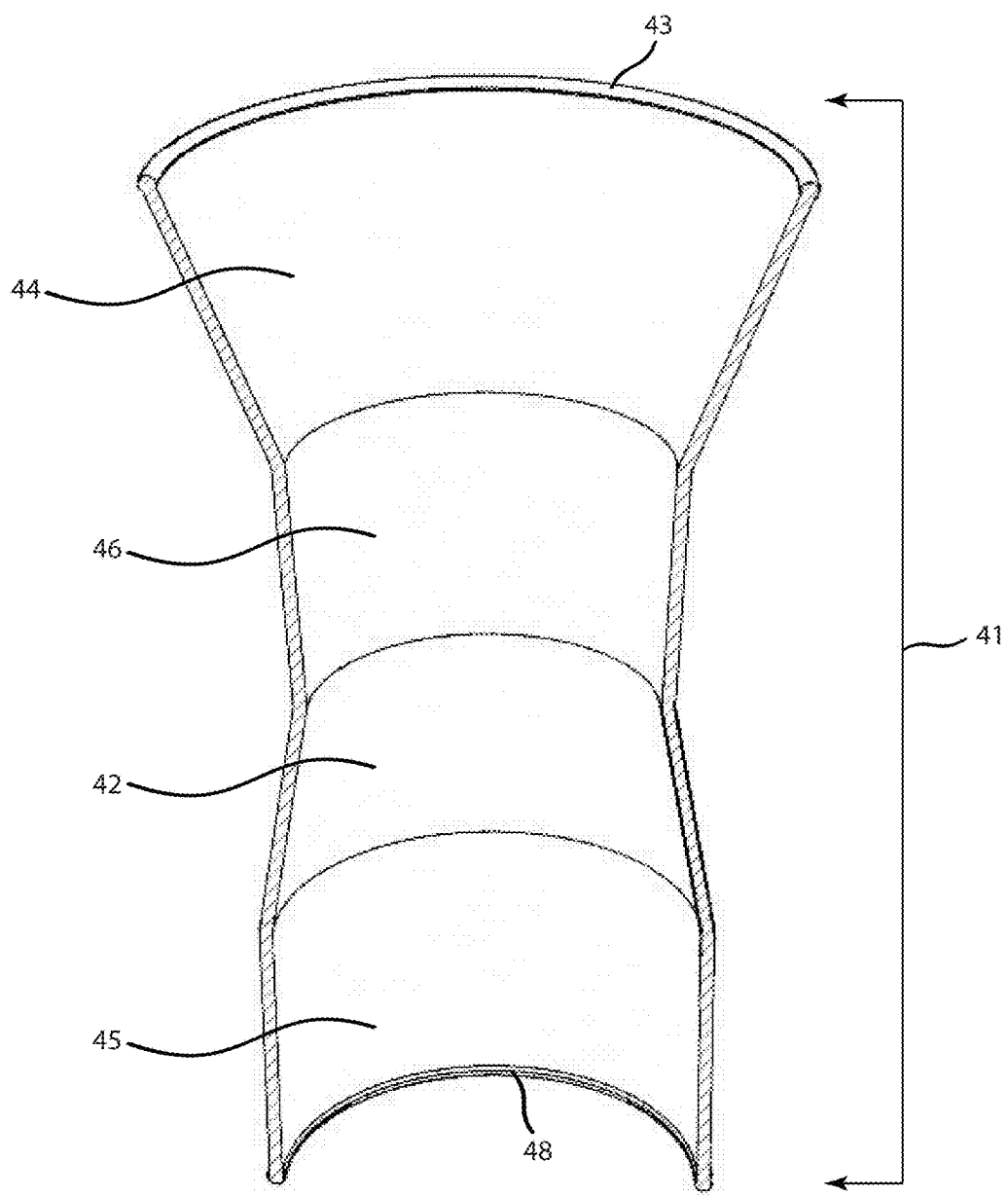
FIG. 5A depicts a cut-away side view of an embodiment of a gel flex air seal 41.
Figure 5B:
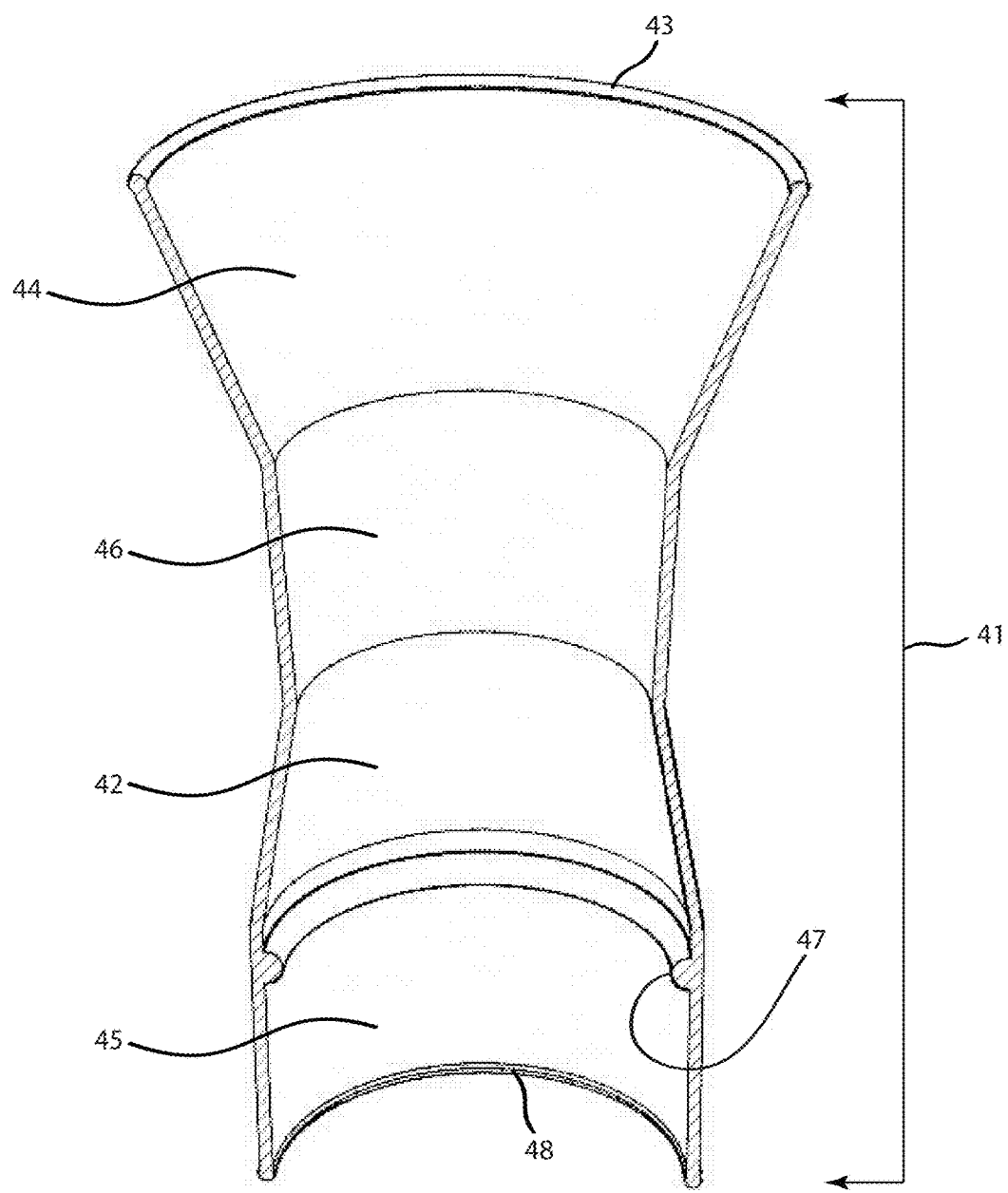
FIG. 5B depicts a cut-away side view of an embodiment of a gel flex air seal 41 with an upper air seal ring 47.

FIG. 5A depicts the interior surface of a gel flex seal 41 that has been cut vertically and spread open. FIG. 5B depicts a cut-away view of an alternative embodiment of a gel flex seal 41 comprising a skirt 45 which includes a lower seal ring 47 that extends three-dimensionally into the tubular cavity of the gel flex seal 41. In application of a skirt embodiment 45 of FIG. 5B, the skirt is stretched and pulled downward over the proximal edge 19 of the frustum until the lower seal ring 47 is pulled past the tubular lip 24 (FIG. 2) of the frustum 18. In addition to the annular tensile force of the skirt 45 around the frustum 118 (which enhances the frictional engagement between the skirt and frustum as discussed above), the lower seal ring 47 abuts against the tubular lip 24. This abutment provides additional resistive force to prevent the traction chamber 7 from pulling free from the gel flex seal 41 when weight or tension is applied to the swivel hook 39.

Figure 5C:
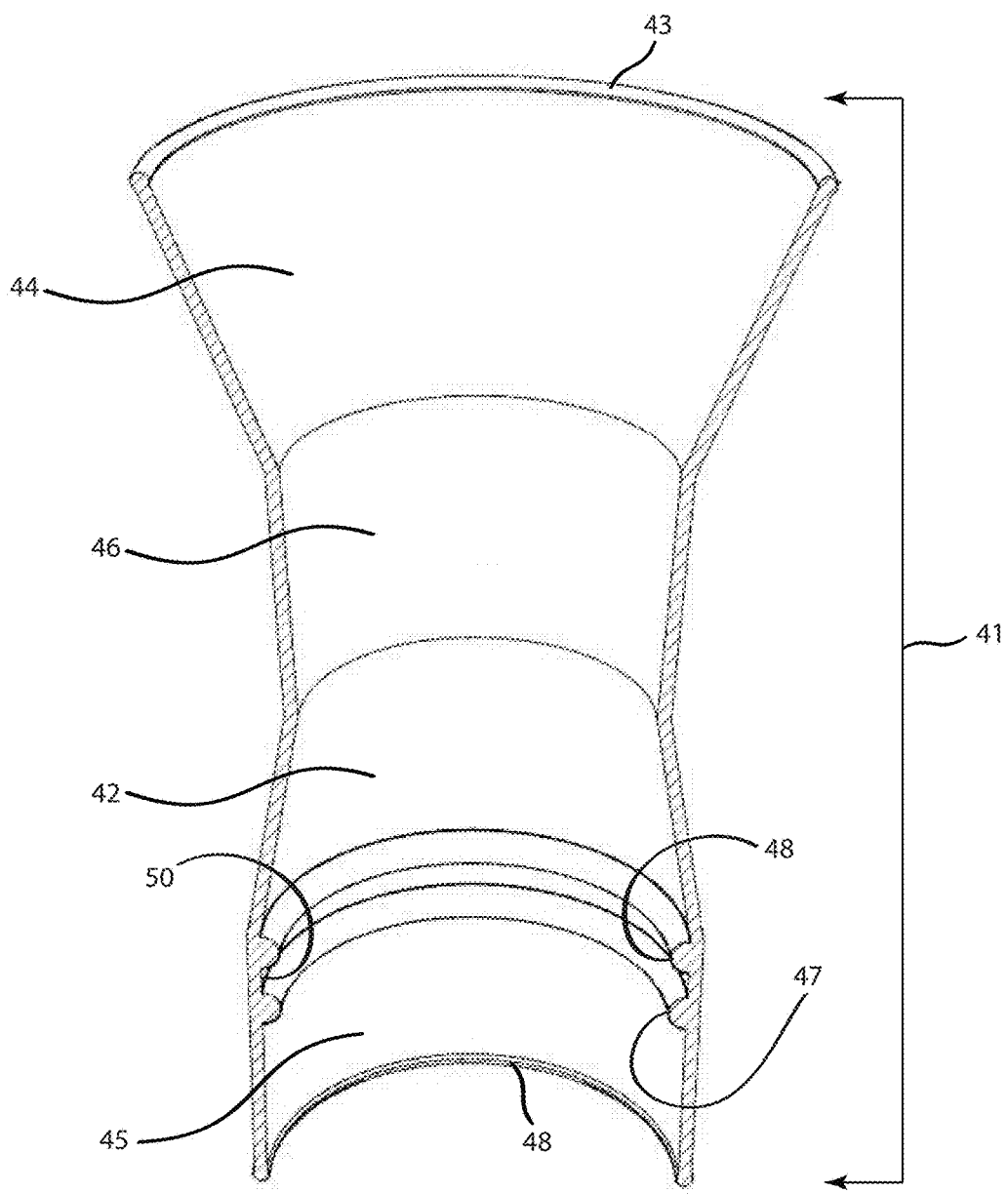
FIG. 5C depicts a cut-away side view of an embodiment of a gel flex air seal 41 having upper and lower air seal rings 47, 48.

FIG. 5C discloses an embodiment of a gel flex seal 41 having a lower ring seal 47 and an upper ring seal 48. Application of the gel flex seal 41 to the frustum 18 is substantially the same in the skirt embodiment of FIG. 5B, wherein the skirt is pulled over the tubular lip 24 of the frustum. In the embodiment of FIG. 5C, however, the distance between the lower ring seal 47 and upper 48 ring seal is configured such that, as the lower ring seal 47 abuts the lower portion of the tubular lip 24, the upper ring seal abuts the upper surface of the tubular lip. The contact between the upper seal ring 48 and the tubular lip enhances the airtight seal, thereby further restricting air from leaking out of the evacuated traction chamber 7.

When air is drawn from the traction chamber 7, the partial vacuum causes the soft, flexible material of the gel flex air seal 41 to collapse inwardly onto the penis 5, forming an air seal the entire length of the spout 44. This enhances the traction which is already exerted by compression of the interior sidewalls walls 11, 25 (FIG. 2) of the traction chamber against the penis 5.

Figure 10:
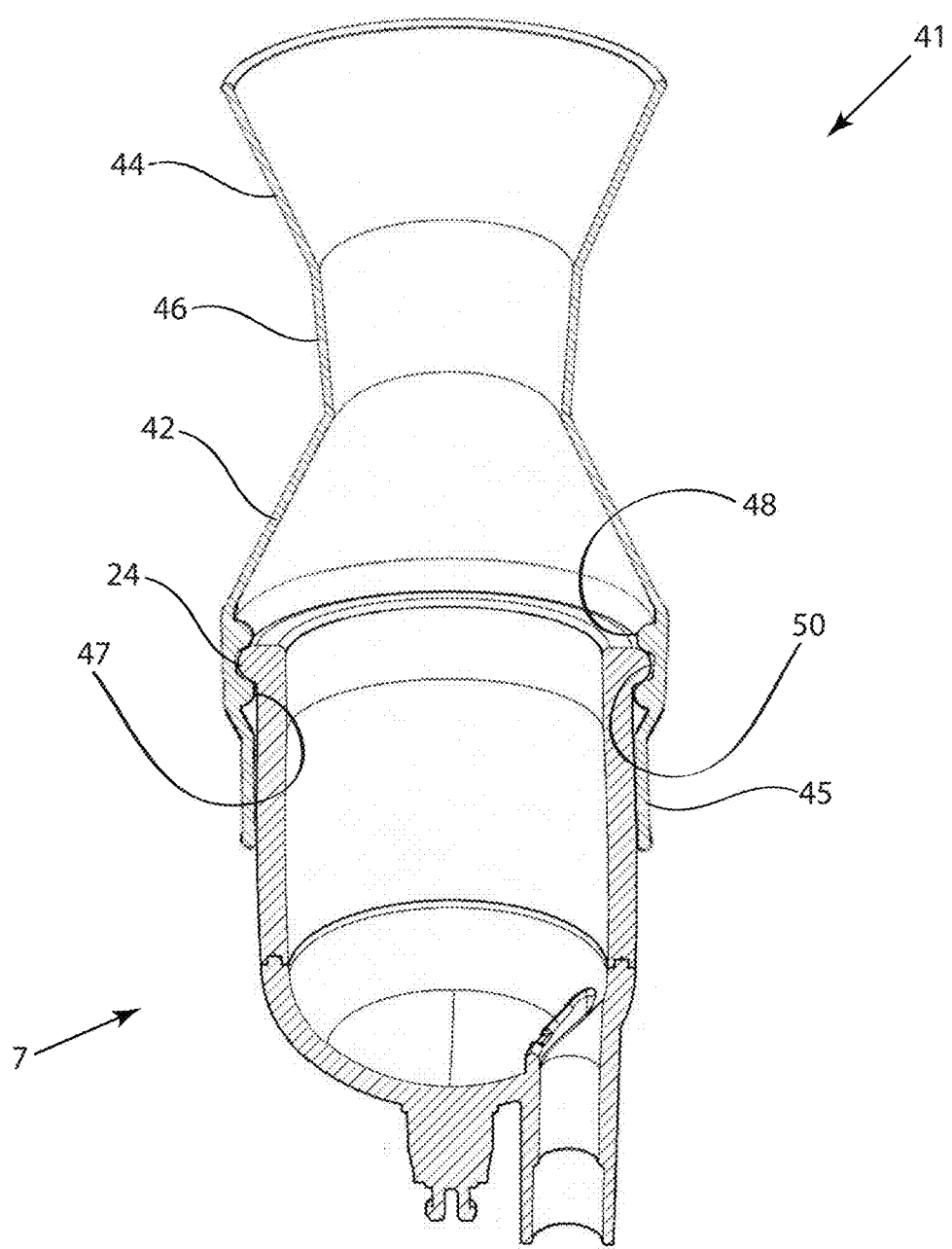
FIG. 10 discloses a cut-away view of the gel flex seal 41 in an assembled state with the traction chamber.

FIG. 10 discloses a cut-away view of the gel flex seal 41 of FIG. 5C in an assembled state with the traction chamber. The lower seal ring 47 abuts the lower edge of the tubular lip 24 of the traction chamber 7, and provides resistive support thereto in order to resist the weight or force applied to the traction chamber from pulling the traction chamber free from the gel flex seal 41. The upper seal ring 48 of the gel flex seal 41 abuts the upper surface of the tubular lip 24 to enhance the airtight integrity between the gel flex seal 41 and the traction chamber 7. The gap 50 between the upper seal ring 48 and the lower seal ring 47 is sized such that the upper and lower seal rings are pulled snugly against the tubular lip 24.

The Standard Gelflex Sleeve

FIG. 1 depicts an embodiment of a standard Gelflex traction sleeve 53 which resembles a condom, but is preferably thicker and more durable than a condom. Although its use in conjunction with the traction device is optional, a preferred embodiment includes the use of the gelflex sleeve 53. The gelflex sleeve is advantageously applied by unrolling it directly onto the penis 5 in a manner similar to that in which a condom is applied. Although it is best to clean the interior daily, when removed and not scheduled for cleaning, it is generally advantageous to unroll the gelflex sleeve to again resemble a packaged condom.

When a user wears a gelflex sleeve 53 in conjunction with the traction device of FIG. 1 or 6, the gel flex traction sleeve 53 is in direct contact with the penis. In view of this, any reference throughout this disclosure to "contact" (or an equivalent term) between the penis 5 (FIG. 1) and the gel flex seal 41 (FIG. 3)—including frictional and/or forcible contact—comprehends indirect contact mediated through the gel flex sleeve 53 which covers the penis. Similarly, any reference within this disclosure to frictional or forcible contact between the penis 5 and the interior sidewalls 11, 25 of the traction chamber 7 also comprehends indirect frictional or forcible engagement which is likewise mediated through the gel flex sleeve 53.

The Swivel Hook Suspended from the Traction Chamber

Referring to FIGS. 1 and 3, the swivel hook 39 is comprised of a rigid material configured to suspend weights therefrom. In the embodiment disclosed in FIG. 2, a snap fixture 38 disposed on the exterior surface 12 of the dome 9 is configured to couple with the a cavity within the neck of the swivel hook 39 (FIGS. 1, 3). The swivel hook is designed to suspend weight(s) 111 therefrom, or alternatively, to couple with the elastic band(s) 58 which impart tension to the apparatus 1. Embodiments are also envisioned which utilize a non-swiveling hook, or other clasp structure suitable for suspending weights from the traction chamber 7. The swivel hook should advantageously be able to suspend at least five times the maximum amount of weight anticipated for actual use. Although the maximum weight will vary from user to user, it is anticipated that 90% of the users will not desire to use more than 10 pounds, and this amount only for short periods. (When a user first begins using the traction chamber, they may only tolerate three to five minutes. However, after several weeks or months, many users will be able to tolerate a ten-pound weight for up to an hour. The term "short period" is therefore relative to the user's endurance.) The reference to specific weights or length of time that the traction chamber is intended only for example, and not intended to be a limitation.

Light-Traction Apparatus

Referring now to FIG. 6, a light-traction embodiment 73 does not utilize a traction chamber 7, but rather, comprises a modified gelflex sleeve 75 configured transmit tensile force without the need for the traction chamber 7 of FIG. 1. The modified gelflex traction sleeve 75 is similar in shape, form, and construction to the standard gelflex traction sleeve 53, but to resist tearing or damage as a result of the tensile force imparted to the tip of the modified gelflex sleeve 75, it is preferably thicker and more durable than the standard gelflex sleeve 53, particularly at the tip, where the tensile force is concentrated.

In use, the modified gel flex traction sleeve 75 is worn in conjunction with the standard gelflex sleeve 53. The standard gelflex sleeve 53 is applied first, and worn directly against the penis 5. The modified gelflex traction sleeve 75 is worn over the standard gel flex sleeve 53. Both advantageously applied from the configuration of a packaged condom and unrolled onto the penis. In the removal process, the modified gel flex sleeve 75 is advantageously rolled back into the configuration of a packaged condom, facilitating ease of reuse.

Figure 7:
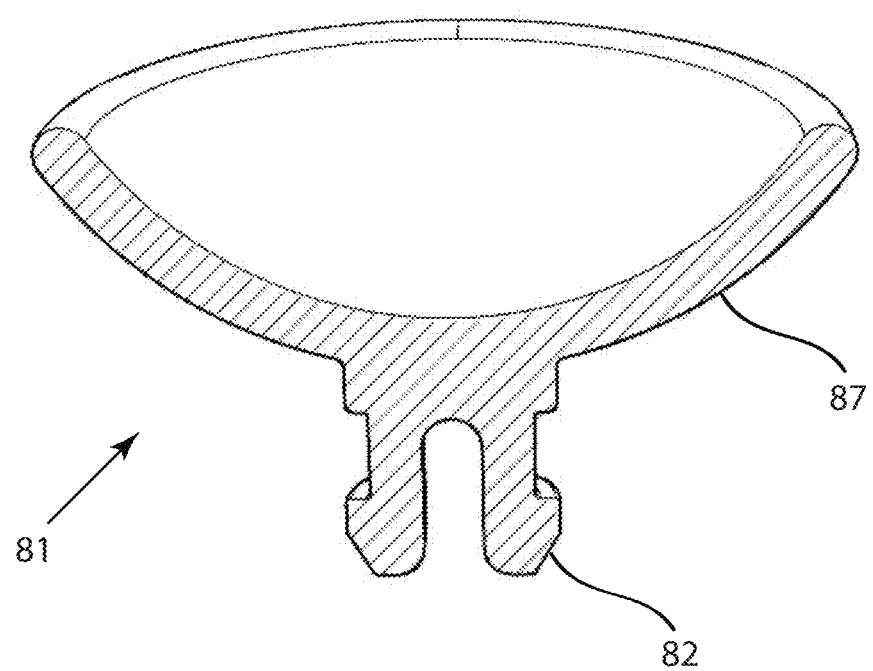
FIG. 7 depicts an embodiment of an inner snap washer 81 for use in the gel flex traction sleeve 75 of the light traction device of FIG. 6.
Figure 8:
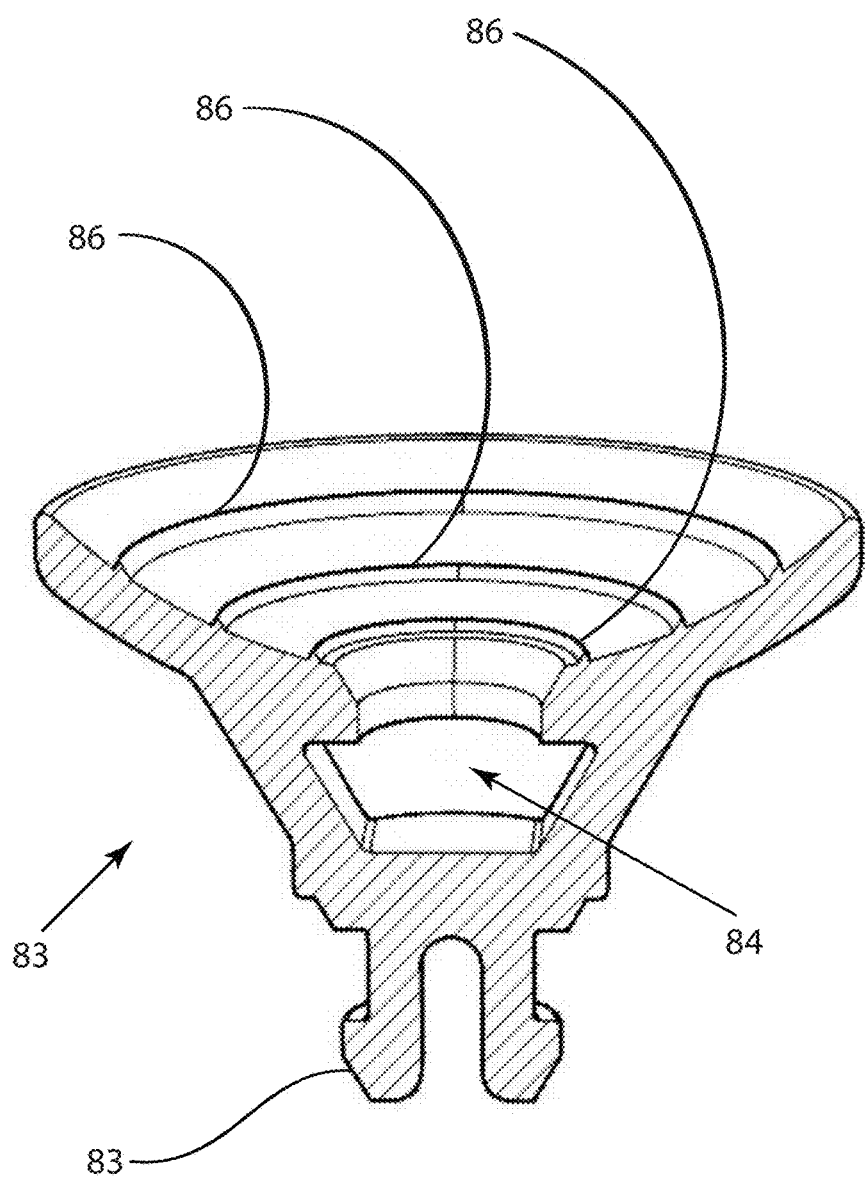
FIG. 8 depicts an embodiment of an outer snap washer 83 for interconnection with the inner snap washer 81 of FIGS. 6 and 7.

Referring to FIGS. 6, 7 and 8, in the fabrication of the light-traction apparatus 73, a puncture hole 79 is formed in the tip 77 of the modified gelflex traction sleeve 75. An inner snap washer 81 has a convex exterior surface terminating at a snap connector 82. The inner snap washer 81 is positioned within the interior of the modified gelflex traction sleeve 75 proximate the puncture hole 79, and the snap connector 82 protrudes through the puncture hole 79. An outer snap washer 83 is disposed proximate the outer tip of the modified gel flex traction sleeve 75. The outer snap washer 83 has a connection expanse 84 for receiving the snap connector 82 of the inner snap washer 81 (FIG. 7) and also has a snap connector 85 for coupling with a swivel hook 88 (FIG. 6).

Still referring to FIGS. 6, 7, 8, the outer snap washer 83 has interlocking ridges 86 formed on its concave interior surface. When the inner and outer snap washers 81, 83 are coupled, the flexible fabric of the modified Gel flex traction sleeve 75 is compressed between the convex exterior surface 87 of the inner snap washer 81 and the interlocking ridges 86 on the outer snap washer, further securing the weight or tension to the traction sleeve 75 and distributing the weight or tension away from the puncture hole 79. In the embodiment depicted in FIG. 8, the interlocking ridges 86 comprise a stair step configuration.

Foot Strap

FIG. 1 discloses a foot strap assembly 59 which advantageously includes a foot loop 61 for attachment to the foot 67 of a user 3. The foot loop 61 extends into an adjustable slide strap 63, which is looped through a loop connector 64. The adjustable slide strap advantageously comprises Velcro portions 69, 71 for securing the end of the slide strap to itself after it is looped through the loop connector 64. The loop connector 64 couples with a foot strap hook 65, which couples with the elastic band 58 to secure the resistive tensile force imparted throughout the traction apparatus. Although the foot strap is illustrated in use with the standard traction device 1 of FIG. 1, it may also be used in conjunction with the light traction device of FIG. 6.

Calf Strap

FIG. 6 discloses calf strap assembly 96 which includes a calf loop 97 that fits around the Soleus muscle 104 of the calf, just below the Gastrocnemius muscle 105 (the larger diamond head area of the calf muscle) thereby preventing the calf loop 97 from slipping upwards. (The soleus muscle 104 and gastrocnemius muscle 105 are collectively referred to herein as the "calf"). The calf strap assembly 96 advantageously comprises complementary Velcro portions 98, 99 for securing the calf-loop 97 in place. The calf strap assembly 96 further includes a rigid connector loop 101 secured to the calf strap assembly 96 by a flexible loop of fabric 100. The members 100, 101 may be permanently joined by stitching, gluing, or some other permanent means of securing fabric. If Nylon is used for the fabric, it can even be fused or melted to permanently join members 100, 101. Alternatively, the rigid connector loop 101 may be secured to the flexible loop of fabric 100 by Velcro members 98, 99 or some other releasable securement means. The rigid connector loop 101 may be coupled with a swivel hook for attachment to an elastic band 58. Alternatively, the rigid connector loop 101 may be coupled to another device, including a clip (not visible) on the housing 92 of the retraction device 91 discussed below.

Retractable Tension Device

FIG. 6 depicts an embodiment of a retractable continuous tension device 91 that may be advantageously used in conjunction with the calf strap assembly 96 and the light traction device (the gel flex traction sleeve 75). The purpose of the continuous traction device 91 is to maintain a continuous tension throughout the device. The continuous tension device 91 comprises a mechanical retraction mechanism 93 (not visible) disposed within a housing 92. The mechanism 93 automatically withdraws a retractable lanyard 94 into the housing 92, thereby maintaining continuous tension on the lanyard. The mechanism 93 of the continuous tension device 91 is analogous to retractable tape measures used by carpenters, and retractable key rings used by janitors. The lanyard 94 terminates at a lanyard ring 95 securely coupled thereto. The lanyard ring 95 can couple a swivel hook 39 disposed at the bottom of the traction chamber 7 of FIG. 1, or to a swivel hook 88 of the light traction embodiment 73 of FIG. 6. The retractable tension device 91 may attach to the calf strap by known means, such as a clip (not visible) on the housing 92 of the device 91. The need for a continual tension device can be readily appreciated by considering that, in daily use, a user may cross his legs, bend his knees, walk, climb stairs, etc. All of these activities will change the tension exerted by an elastic band. A continuous tension device circumvents this limitation.

To prevent chaffing or annoying contact against the calf of the user 3 by the rigid connector loop 101 or the housing 92 of the retraction device 91, the calf strap assembly 96 (FIG. 6) advantageously includes a protective shield 102 extending upward from the calf loop 97. The protective shield 102 preferably comprises a rigid or semi rigid material, but preferably includes a fabric or other soft non-irritating lining 103 for contact with the skin of the user 3.

The depiction of the continuous tension device 91 with the traction sleeve 75 of FIG. 6 is not intended to limit the application of the continuous tension device. Applications are fully envisioned for use of the continuous tension device in conjunction with other traction device embodiments, including, but not limited to, the traction chamber 7 embodiment of FIG. 1. In a similar manner, a tension band embodiment 58 such as depicted in FIG. 1 is fully envisioned for use in conjunction with a calf strap embodiment 96 of FIG. 6, or either of the gel flex traction sleeve 75 or 115 of FIG. 6. Any combination of weights, tension bands and continuous tension devices may be used simultaneously.

Embedded Weight Embodiment

FIG. 6 depicts an alternative light traction device 114 utilizing a standard gel flex sleeve 53 worn on the penis of the user, and a second sleeve 115, which may be a standard sleeve 53 or a more durable modified gel flex traction sleeve 75. In any configuration, a weight 106 lodged in the tip of the second sleeve 115. Although the application of the alternative light traction embodiment 114 is not limited to any particular weight, it is believed that weight or forcible tension in the range of 1 to 1½ pounds is most suitable for most users. In an embodiment, the weight may be formed from a heavy metal and embedded within layers of rubber or other material at the tip of the traction device. Some of the densest metals which may be used to form a compact weight include osmium (22.61 g/cm$^3$), iridium (22.56 g/cm$^3$), platinum (21.4 g/cm$^3$), gold (19.3 g/cm$^3$), tungsten (19.3 g/cm$^3$), palladium (12.16 g/cm$^3$), lead (11.4 g/cm$^3$) and silver (10.49 g/cm$^3$). Although many of the foregoing are priced as precious metals valued at hundreds of dollars per ounce, tungsten is available for approximately one dollar per ounce, making it an attractive alternative in most user markets. By using an extremely dense metal, a weight of approximately 1½ pounds can be compressed into a comparatively small area, making it practical to wear the light traction device under one's clothing throughout the day, whether at work, the market, etc. In an embodiment, the second sleeve 115 has a layered tip in which the weight is completely sealed within a pocket at the tip of the sleeve, eliminating the need to clean the weight between applications.

Method for Fitting

Because it is preferable not to induce engorgement of the erectile tissues for excessive periods of time, or otherwise expose the penis to a partial vacuum for prolonged periods, it is preferable that the penis 5, in its flaccid state, is just barely able to fit into the frustum 18. This ensures that, when the air in the frustum is evacuated, the penis will forcibly engage the sidewalls of the frustum before the penis experiences excessive swelling or engorgement. Therefore, in a preferred embodiment, the frustum should be sized only slightly larger than the diameter of a flaccid penis under tension. Referring to FIG. 2 briefly, according to an embodiment, the diameter D2 of the opening 20 of the frustum 17 should be no more 30 mm greater than the diameter of the flaccid penis, and more preferably no more than 15 mm greater than the diameter of the flaccid penis under tension, and even more preferably no more than 5 mm greater than the diameter of the flaccid penis under tension. However, embodiments are envisioned in which the diameter D2 of the opening 20 of the frustum 18 is larger than the diameter of the flaccid penis by more than 30 mm.

The following steps will enable a user to order a frustum of optimal diameter: 1) hold the flaccid penis near the glans and pull downward with a firm, continual tension. 2) Measure the diameter or circumference of the flaccid penis in this tensile state. [Hereinafter the "measured diameter" or "measured circumference"]. A circumferential measurement can be achieved by taking a graduated string and wrapping it around the penis, noting the measured circumference, or using a linear caliper to measure the diameter of the flaccid penis under tension, and a second measurement made without tension. 3) Submit the measured diameter (or measured circumference) with an order for a traction device. 4) Select a traction device in which the diameter of the opening of the frustum 18 (the diameter of the proximal opening 20) is chosen according to the measured diameters or measured circumferences reported by the user.

Usage

The following steps describe usage of the traction chamber embodiment of the traction apparatus of FIG. 1: i) stretching the gel flex air seal 41 over the opening 20 of the traction chamber 7 (FIGS. 2, 3); ii) aligning the lower and upper gel flex air seal rings 47, 49 to abut opposite sides of the tubular lip 24 of the traction chamber 7 (FIG. 10) to secure the gel flex air seal 41 in place; iii) attaching the vacuum nipple 57 to the vacuum hose 55 (FIG. 9); iv) attaching the vacuum hose 55 to the vacuum pump 56 (FIG. 9); v) coupling the vacuum pump nipple 57 with the airlock port 28 of the traction chamber 7 (FIGS. 3, 4, 9); vi) arranging the gel flex traction sleeve 53 into a "rolled" configuration for easy application; vii) unrolling the gel flex traction sleeve 53 onto the penis—or otherwise applying the gel flex traction sleeve 53 to the penis 3 (FIG. 1); viii) arranging at least a portion of the gel flex air seal 41 into a "rolled" configuration for easy application. ix) inserting the penis 3 through the gel flex air seal 41 and into the traction chamber 7 (FIGS. 1, 3, 10); x) rolling the gel flex air seal 41 up over the length of the penis 3—or otherwise extending the gel flex air seal 41 up over the penis (FIGS. 1, 3, 10); xi) securing the gel flex air seal 41 against the penis 3 by a hand while actuating the vacuum pump 56 (FIG. 9) to form a partial vacuum in the traction chamber 7; xii) disconnecting the vacuum nipple 57 from the airlock port of the traction chamber 7 (FIGS. 3, 4, 9); xiii) suspending a weight 111 or tension band 58, or continuous tension device 91 (FIGS. 1, 6) from the swivel hook 39.

Method for Dual Usage

Optimal lengthening of the penis may be achieved by interchangeably using the "heavy" traction device 1 of FIG. 1 (the traction chamber embodiment) for one or more short intervals every day, and alternatively using one of the light traction embodiments 73, 114 of FIG. 6 for longer periods throughout the day. For example, at the beginning of the day, a user can wear the "heavy" traction device 1 of FIG. 1 with a tension of ten pounds while shaving, brushing his teeth, and so forth, for a period of twenty minutes. (Although "short duration" varies from user to user, upon initial use of the apparatus, three minutes may be excessive. After becoming acclimated to the heavy traction device, a user may be able to use the heavy-traction device for up to an hour with a weight of ten pounds. The term "short duration" is therefore flexible relative to the user). The user will then remove the traction chamber 7, and use a light traction embodiment 73, 114 with a smaller weight or tension (e.g. 1½ lb), for an extended period, such as ten hours during the work day. In the evening, the user 3 again wears the heavy traction device for a limited period (from three minutes up to one hour) before retiring. While sleeping, the user again wears the light traction device 73 with a calf strap embodiment with one or two pounds of tension. Alternating between the "heavy traction" and "light traction" embodiments maintains tensile force on the penis, thereby producing greater and more rapid lengthening of the penis than using only one of the embodiments.

The recitation herein of certain dimensions, angles, components and alternative embodiments are offered for exemplary purposes only, and have not been depicted to limit the application of the traction devices described herein, which fully comprehend alternative embodiments within the spirit and scope of the specification and drawings.

What is claimed is:

1. An apparatus for exerting a tensile force on a penis, the apparatus comprising:
   a) a traction chamber with an interior surface extending continuously from a proximal end to a distal end, the traction chamber comprising a tubular section extending from a primary opening at the proximal end and coalescing into an enclosed end-piece that extends to the distal end of the traction chamber, a distal end of the tubular section also representing a proximal end of the end-piece, wherein the interior surface of the tubular section comprises tapered interior sidewalls, a taper such that an interior diameter of the tubular section progressively increases from the primary opening to the distal end of the tubular section, the taper configured such that, when the penis is disposed within a partially evacuated traction chamber, an entire surface area of the interior surface of the tubular section transmits a compressive force against the penis;
   b) a valve coupled with the traction chamber, the valve configured to releasably couple with a vacuum device configured to draw air from the traction chamber;
   c) a flexible air tight seal comprising a tubular configuration with a skirt forming a distal segment of the tubular configuration, wherein, when the apparatus is in an assembled state, the skirt is stretched under tension to cover the primary opening of the traction chamber, and wherein tension within the skirt urges it to adhere against an exterior surface of the traction chamber to form an air tight abutment between the skirt and the traction chamber;
   d) a hook coupled to the traction chamber and structurally configured to transmit a tensile force to the traction chamber.

2. An apparatus for exerting a tensile force on a penis, the apparatus comprising:
   a) a traction chamber with an interior surface extending continuously from a proximal end to a distal end, the traction chamber comprising a tubular section extending from a primary opening at the proximal end and coalescing into an enclosed end-piece that extends to the distal end of the traction chamber, a distal end of the tubular section also representing a proximal end of the end-piece, wherein the interior surface of the tubular section comprises tapered interior sidewalls, a taper such that an interior diameter of the tubular section progressively increases from the primary opening to the distal end of the tubular section, the taper configured such that, when the penis is disposed within a partially evacuated traction chamber, an entire surface area of the interior surface of the tubular section transmits a compressive force against the penis;
   b) a valve coupled with the traction chamber, the valve configured to releasably couple with a vacuum device configured to draw air from the traction chamber;
   c) a hook coupled to the traction chamber and structurally configured to transmit a tensile force to the traction chamber.

3. The apparatus according to claim 2, wherein a taper of the interior sidewalls defines a conic frustum.

4. The apparatus according to claim 3, wherein opposing interior sidewalls are tapered at an angle of intersection of less than 15°.

5. The apparatus according to claim 4, wherein opposing interior sidewalls are tapered at an angle of intersection of less than 5°.

6. The apparatus according to claim 2, wherein a taper of the interior sidewalls comprises a nonlinear taper.

7. The apparatus according to claim 2, wherein a linear distance from the proximal end of the tubular section to the distal end of the tubular section is between 2.3 cm and 8.3 cm.

8. The apparatus according to claim 2, wherein a linear distance from the proximal end of the tubular section to the distal end of the tubular section is between 3.5 cm and 4.5 cm.

9. The apparatus according to claim 2, wherein the closed end-piece comprises a concave dome-shaped interior surface configured to interface with a glans-penis inserted there-against.

10. The apparatus according to claim 2, wherein the traction chamber comprises a rigid material.

11. The apparatus according to claim 2, wherein, the end-piece includes a tapered section configured to lock onto the glans penis in a partial vacuum in which the glans penis expands.

12. The apparatus according to claim 11, wherein the tapered section of the end-piece commences at the proximal end of the end-piece and extends part way to the distal end of the traction chamber, wherein a cross-sectional diameter at the proximal end of the end-piece is smaller than a cross-sectional diameter of the interior section of the end piece at the distal edge of the tapered section.

13. The apparatus according to claim 2, wherein the hook is a swivel hook.

14. The apparatus according to claim 2, further comprising a flexible air tight seal comprising a tubular configuration with a skirt forming a distal segment of the tubular configuration, wherein, when the apparatus is in an assembled state, the skirt is stretched under tension to cover the primary opening of the traction chamber, and wherein tension within the skirt urges it to adhere against an exterior surface of the traction chamber to form an air tight abutment between the skirt and the traction chamber.

15. The apparatus according to claim 14, wherein the exterior surface of the traction chamber comprises a tubular lip at the proximal edge of the traction chamber, and wherein a portion of the flexible air tight seal extends over the tubular lip.

16. The apparatus according to claim 15, wherein the tubular lip has a proximal edge substantially coterminous with the proximal end of the traction chamber, and a distal edge that intersects a cylindrical exterior surface of the traction chamber, and wherein the flexible air tight seal comprises a lower air seal ring that abuts the distal edge of the tubular lip.

17. The apparatus according to claim 16 wherein the flexible air tight seal further comprises an upper air seal ring that abuts the proximal edge of the tubular lip.

18. The apparatus according to claim 17, further comprising a gel flex sleeve configured to be worn over the penis, wherein, in actual use, contact between the penis and the sidewalls of the traction chamber is an indirect contact mediated through the gel flex sleeve.

19. The apparatus according to claim 18, further comprising means for applying tension to the traction chamber while it is worn on the penis of a user, said means selected from among a group consisting of a weight, an elastic member, and a combination thereof.

20. An apparatus for applying a tensile force to a penis, the apparatus comprising:
   a) a traction chamber configured to cover at least a portion of a penis, said traction chamber having sidewalls forming a frustum-shaped segment with a proximal end and a distal end, the traction chamber terminating at a dome shaped cover coupled to, and extending outward from, the distal end of the frustum-shaped segment, wherein the distal end of the frustum-shaped segment has a greater diameter than the proximal end of the frustum-shaped segment; and,
   b) a clasp coupled to the traction chamber, said clasp structurally configured to suspend a weight therefrom.

* * * * *